United States Patent [19]
Noon et al.

[11] Patent Number: 4,731,076
[45] Date of Patent: Mar. 15, 1988

[54] PIEZOELECTRIC FLUID PUMPING SYSTEM FOR USE IN THE HUMAN BODY

[75] Inventors: George P. Noon; Louis W. Feldman; Paul I. Weiss; Michael E. DeBakey, all of Houston, Tex.

[73] Assignee: Baylor College of Medicine, Houston, Tex.

[21] Appl. No.: 944,100

[22] Filed: Dec. 22, 1986

[51] Int. Cl.⁴ .................... A61F 2/22; A61M 1/10; A61H 1/02; A61H 7/00
[52] U.S. Cl. .................................. 623/3; 623/2; 128/1 D; 128/25 R; 128/64; 128/DIG. 3; 417/322; 417/412; 417/413
[58] Field of Search .............. 623/3, 24, 2, 14, 26; 128/1 D, 25 R, DIG. 3, 64, DIG. 25; 417/322, 412, 413

[56] References Cited

U.S. PATENT DOCUMENTS

| | | | |
|---|---|---|---|
| 3,425,064 | 2/1969 | Carnevale et al. | 623/3 |
| 3,478,737 | 11/1969 | Rassman | 128/64 |
| 3,568,214 | 3/1971 | Goldschmied | 623/3 |
| 3,636,570 | 1/1972 | Nielson | 623/3 |
| 3,857,382 | 12/1974 | Williams, Jr. et al. | 417/322 X |
| 3,963,380 | 6/1976 | Thomas, Jr. et al. | 623/3 X |
| 4,493,314 | 1/1985 | Edwards, II | 623/3 X |
| 4,536,893 | 8/1985 | Parravicini | 623/3 |
| 4,621,617 | 11/1986 | Sharma | 623/3 X |

OTHER PUBLICATIONS

The Piezoelectric Artificial Heart, by M. L. Loehr et al., vol. X, Trans. Amer. Soc. Artif. Internal Organs, 1964, pp. 147-150.
The Design of a Piezoelectric Heart Assist Device, Williams et al., I.E.E.E. Transactions on Biomedical Engineering, vol. BME 22, pp. 40-45, Jan. 1975.

*Primary Examiner*—Ronald L. Frinks
*Attorney, Agent, or Firm*—Fulbright & Jaworski

[57] ABSTRACT

A totally or partially implantable fluid delivery system actuated by a valveless piezoelectric drive system. The drive system may actuate an artificial heart by a hydraulic bladder or directly actuate a human heart. The drive system has an output with a frequency and displacement sufficient to directly drive a human or artificial heart and includes a control circuit for recapturing and reusing the power driving the piezoelectric drive system. An artificial heart which includes two check valves having a flexible valve element and supporting tabs on opposite sides.

18 Claims, 12 Drawing Figures

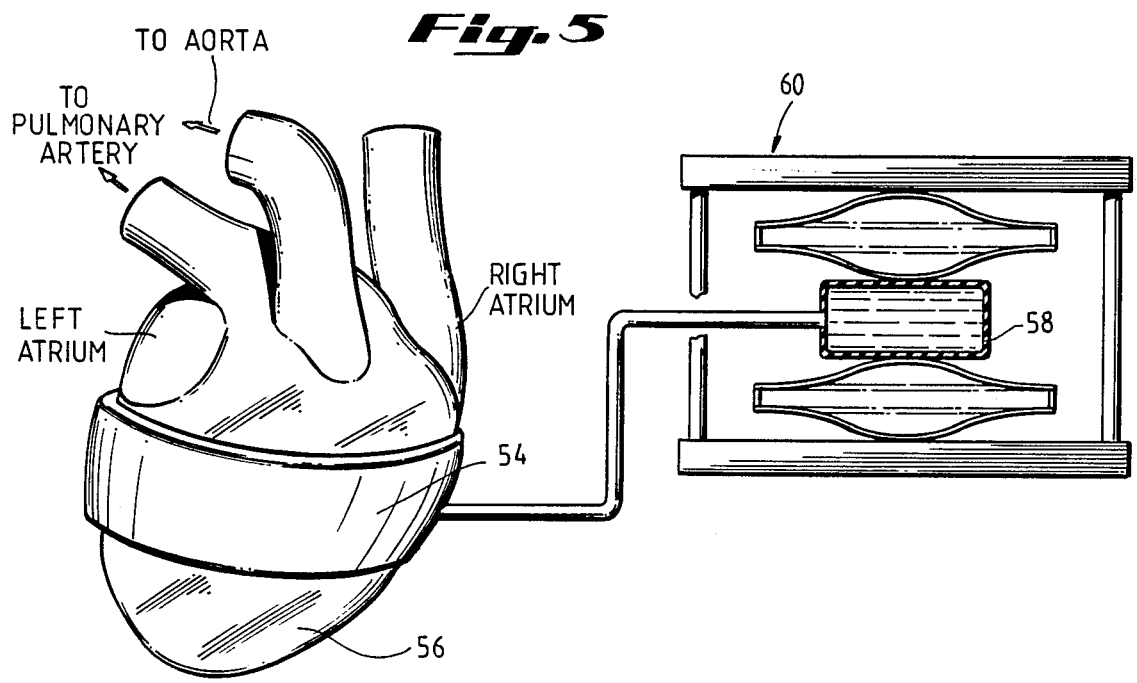
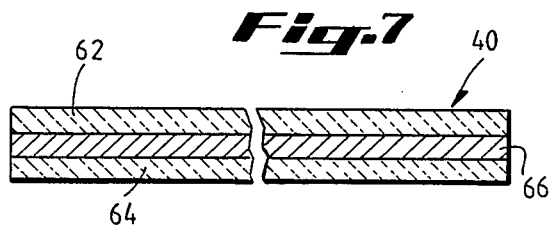
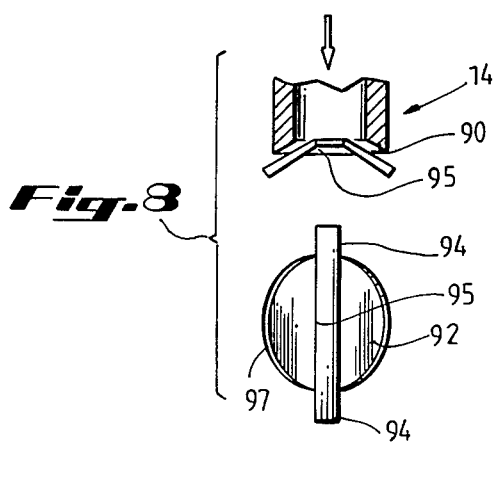
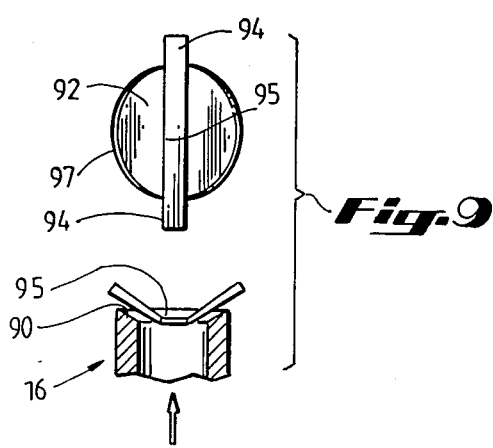

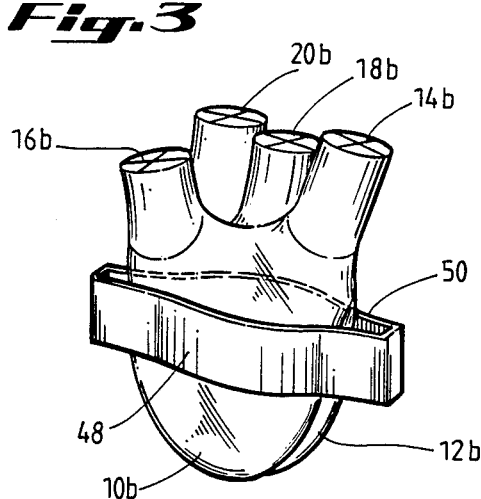
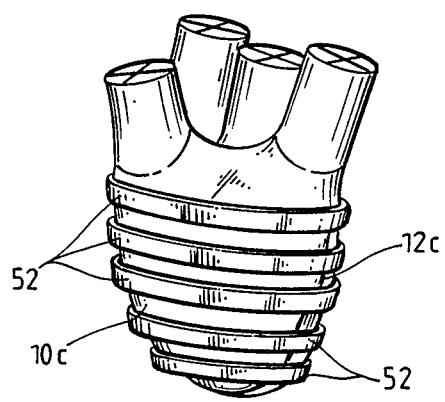
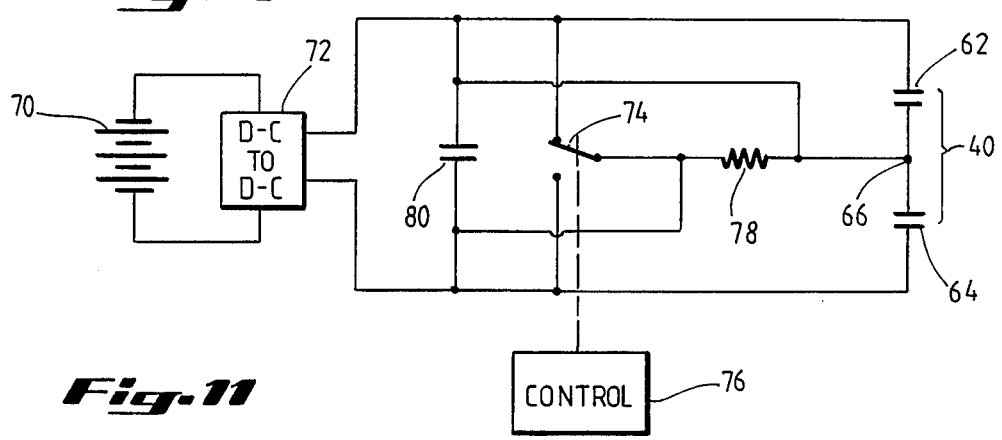
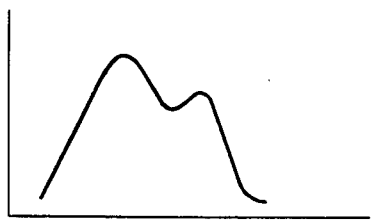
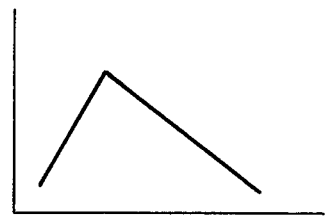

PIEZOELECTRIC FLUID PUMPING SYSTEM FOR USE IN THE HUMAN BODY

BACKGROUND OF THE INVENTION

The concept of using a piezoelectric motor to power heart assist devices or artificial hearts has been suggested in the past. Piezoelectric devices have the advantage of low power requirements, little heat dissipation and little noise as compared with other types of electrical, pneumatic, or mechanical drive systems. Nevertheless, piezoelectric drive systems have not been successful in pumping human blood systems because the output frequency, pressure, and displacement were not compatible with the requirements of a human or artificial heart. Therefore, these previous devices required auxiliary equipment such as valves to produce the desired output thereby adding to the size, additional controls and power requirements, none of which has proved practical.

The present invention is directed to an improved valveless piezoelectric drive system and its use in actuating various types of fluid systems in a human body.

SUMMARY

One feature of the present invention is directed to a fluid delivery system for use in a human body which includes a hydraulic bladder connected to and actuated by a hydraulic pump. A valveless piezoelectric drive system is connected to and drives the hydraulic pump for expanding and releasing the bladder. A battery and a DC to DC converter provides the power to the piezoelectric drive system for miniaturizing but providing an efficient power source. The efficiency of the piezoelectric drive system is increased by providing means for recapturing and reusing some of the electrical power driving the piezoelectric drive system.

Still a further object of the present invention is wherein the recapturing and reusing power means includes a resistor through which the piezoelectric system is discharged to provide a charging voltage across a capacitor for driving the piezoelectric system during the driving cycle.

Yet a still further object of the present invention is wherein control means are provided for actuating the piezoelectric drive system which includes switching means providing an output pressure wave shape simulating a heart wave which is advantageous in pumping blood in the human body as distinquished from a conventional sinusoidal type wave form.

Still a further object of the present invention is the provision of an implantable blood pump including an artificial heart, a hydraulic bladder connected to the exterior of the artificial heart for contracting and releasing the heart in response to hydraulic pressure and a hydraulic pump connected to the hydraulic bladder. A valveless piezoelectric drive system is connected to and drives the hydraulic pump and the system has a frequency in the range of 60 to 120 cycles per minute and provides a hydraulic flow rate of approximately eight liters per minute.

Still a further object is the provision of an artificial heart which includes first and second check valves in which each valve includes a valve seat, a flexible valve element, and two supporting tabs. The tabs are connected to opposite sides of the valve element and connected to the valve seat and act to prevent the valve element from being pushed through the seat. Preferably the valve elements are circular.

A further object is wherein the piezoelectric drive system includes an elongate piezoelectric plate on opposite sides of the heart. In another embodiment the piezoelectric drive system includes a plurality of piezoelectric fibers encircling the heart and positioned parallel to each other.

A still further object of the present invention is the provision of an implantable pump for actuating a human heart which includes a hydraulic bladder surrounding the exterior of the heart for contracting and releasing the heart in response to hydraulic pressure and connected to a hydraulic pump. A valveless piezoelectric drive system is connected to and drives the hydraulic pump and the system includes an output suitable for directly driving the pump, the bladder and heart.

Other and further objects, features and advantages will be apparent from the following description of presently preferred embodiments of the invention, given for the purpose of disclosure and taken in conjunction with the accompanying drawings.

BRIEF DESCRIPTION OF THE DRAWINGS

FIG. 3 is a schematic of an implantable artificial heart driven directly by the piezoelectric drive system, FIG. 4 is another embodiment of a totally implantable artificial heart employing piezoelectric drive system having a plurality of piezoelectric fibers, FIG. 5 is a piezoelectric drive system connected to and compressing and releasing a natural heart, FIG. 6 is a top view of the preferred embodiment of one of the piezoelectric drive plates, FIG. 7 is a side view of the apparatus in FIG. 6, FIGS. 8 and 9 are schematic elevational and top views of a preferred form of check valve used in an artificial heart, FIG. 10 is an electrical schematic of the drive circuit for the piezoelectric plates, and FIGS. 11 and 12 are the wave form output of a human heart and the wave form output of the present drive system, respectively.

DESCRIPTION OF THE PREFERRED EMBODIMENTS

While the present invention will be described in connection with a piezoelectric drive system for actuating an artificial or a natural heart or as a heart assist device, for purposes of illustration only, the present valveless piezoelectric drive system may be used with various other types of fluid delivery systems for use in the human body.

Figure 1:
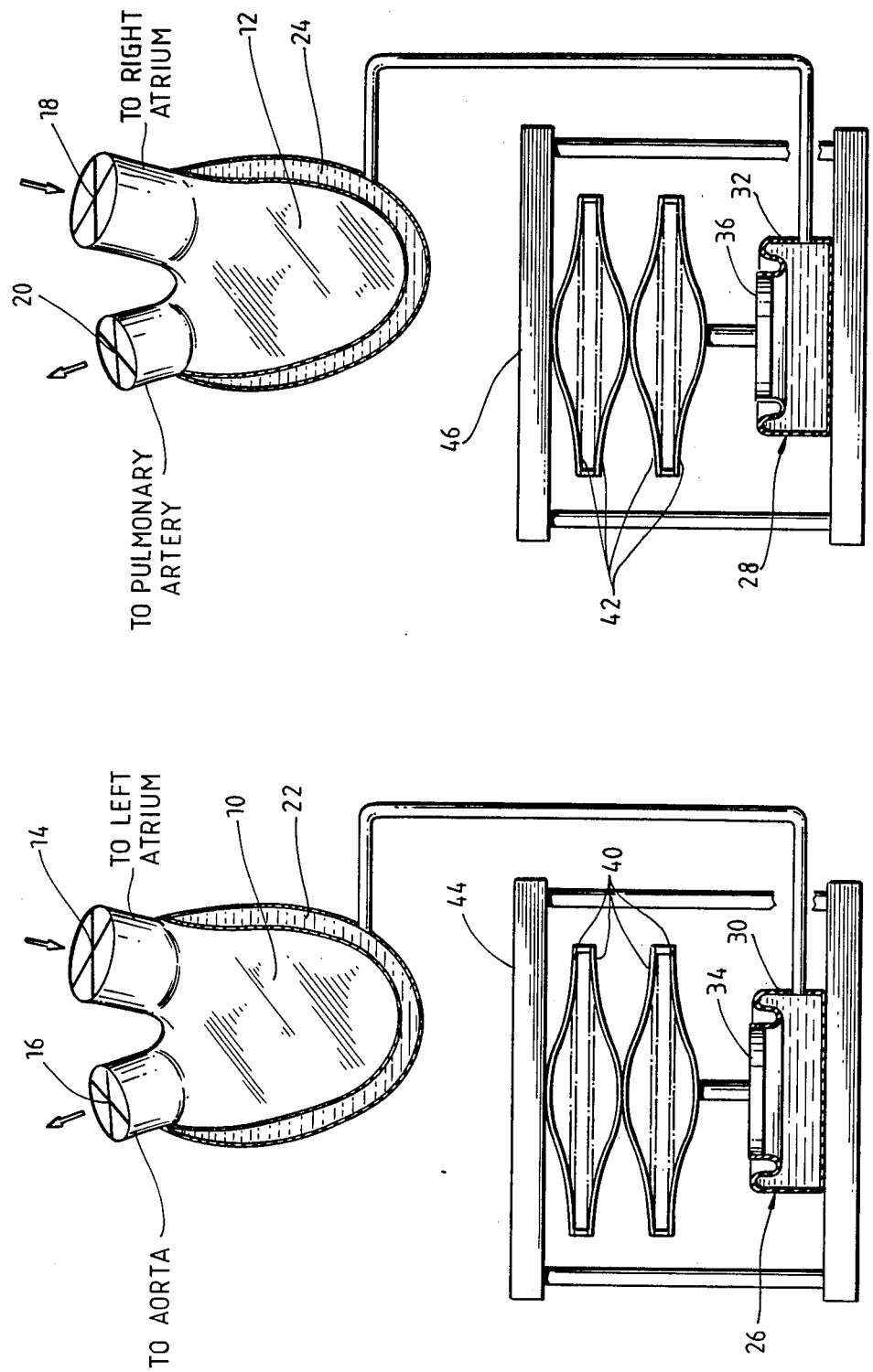
FIG. 1 is a schematic of one form of an implantable artificial heart of the present invention.

Referring now to the drawings and particularly to FIG. 1, the reference numeral 10 generally indicates an artificial left heart and the reference numeral 12 generally indicates an artificial right heart. Preferably, the left heart 10 and the right heart 12 are flexible bladders of a size and shape similar to natural hearts for implantation into a body. The hearts 10 and 12 may be of any suitable material. For example, a material such as segmented polyurethane sold under the trademark Mitrathane may be used. Each of the hearts includes an inlet and an outlet check valve. Thus heart 10 includes an inlet valve 14 in the left atrim and an outlet check valve 16 which is placed in communication with the aorta. Similarly, the right heart 12 includes an inlet check valve 18 in the right atrim and an outlet check valve 20 in communication with the pulmonary artery. The valves 14, 16, 18 and 20 may be of any conventional type valve, but a preferred embodiment will be described hereinafter.

An outer hydraulic bladder 22 is connected to the exterior of the left heart 10 and an outer hydraulic bladder 24 is connected to the exterior of the right heart 12. The bladders 22 and 24 are for the purpose of contracting and releasing the hearts 10 and 12, respectively, in response to hydraulic pressure. The outer bladders 22 and 24 may be of any suitable material such as polyurethane or silicone.

A first hydraulic pump 26 is connected to the outer bladder 22 and a second hydraulic pump 28 is connected to the second bladder 24. The pumps 28 and 30 may be of any suitable form such as having a housing 30 and 32, respectively, and a movable diaphragm 34 and 36, respectively.

One of the features of the present invention is the use of a valveless piezoelectric drive system for driving the pumps 26 and 28. A piezoelectric drive system is highly advantageous over other types of drive systems in that a piezoelectric drive system is smaller, less weight, noiseless, has a lower power consumption and less heat output. However, piezoelectric drive systems require high voltages and low outputs and therefore generally require auxiliary equipment such as transformers and valves which counteracted the desirable characteristics of the piezoelectric drive. Preferably, in order to obtain a larger output, the piezoelectric elements are stacked together. Thus a plurality of piezoelectric elements, here shown as four, which are numbered 40 drive the hydraulic pump 42 and a plurality of elements 42 drive the pump 28. The concave and convex alternating deflection of the elements 40, when they are electrically actuated, is applied to the diaphragm 34 by being connected to a suitable support 44. Similarly, a support 46 transfers the alternating concave and convex motion of the piezoelectric elements 42 to the diaphragm 36. A more detailed description of the piezoelectric elements 40 and 42 will be described hereinafter. However, by electrically actuating the elements 40 and 42, the pumps 26 and 28 may be operated to supply hydraulic fluid to and from the outer bladders 22 and 24, respectively, to operate the artificial hearts 10 and 12.

While the system shown in FIG. 1 is shown as operating both the left heart 10 and the right heart 12, a half system may be used for actuating only one of the hearts. That is, it is common to implant only a left heart only for a left ventricle assist.

Figure 2:
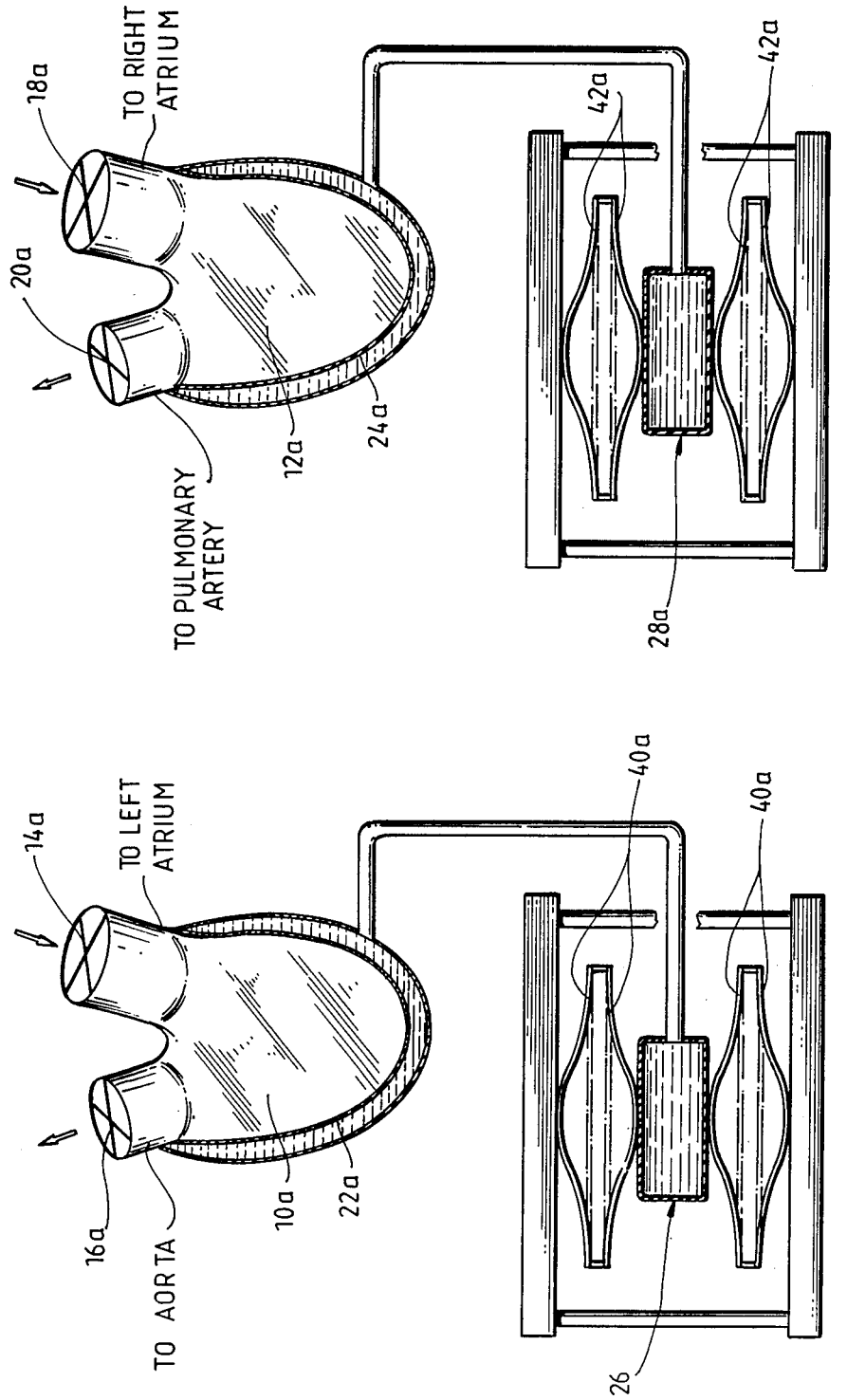
FIG. 2 is a schematic of an implantable artificial heart with a different arrangement of the piezoelectric drive system.

Referring now to FIG. 2, other embodiments of the present invention are shown similar to that in FIG. 1 wherein like parts are similarly numbered with the addition of the suffix "a". The system of FIG. 2 differs in that the pumps 26a and 28a are merely flexible chambers and two of the piezoelectric elements are positioned on opposite sides of the pumps 26a and 28a, respectively, for obtaining the desired output.

Another embodiment of the present invention is best seen in FIG. 3 wherein the left artificial heart 10b and the right artificial heart 12b are actuated directly by the piezoelectric drive system by omitting the outer bladders and the hydraulic pumps. In this embodiment, piezoelectric drive systems consist of elements 48 and 50 which directly engage the exterior of the hearts 10b and 12b for contracting and releasing the hearts 10b and 12b for pumping blood through the check valves 14b, 16b, 18b, and 20b.

Referring now to FIG. 4, one or more artificial hearts 10c and 12c are shown in which the hydraulic outer bladder and hydraulic pumps are omitted. In this embodiment the hearts 10c and 12c are contracted and released by a plurality of piezoelectric fiber elements 52 which encircle the hearts and are positioned parallel to each other. These fiber elements 52 will act generally in a manner similar to that of the heart muscles in that they will contract and expand upon being actuated by a piezoelectric drive system. The elements are available under the trademark "Kynar" sold by Pennwalt Corporation.

Referring now to FIG. 5, another embodiment is shown in which a valveless piezoelectric drive system is used to actuate a natural heart. Thus, a hydraulic bladder 54 is connected around the exterior of the natural heart 56 for contracting and releasing the heart 56 in response to hydraulic pressure. A hydraulic pump 58 is connected to the bladder 54 and in turn is actuated by a piezoelectric drive system generally indicated by the reference numeral 60 which is similar to that shown in FIG. 2. This particular embodiment is useful in those cases in which the valves of the natural heart are satisfactory and are not in need of replacement.

Referring now to FIGS. 6 and 7, the top and side view of one of the piezoelectric elements such as 40 or 42 here shown as 40 is best seen. The element 40 consists of top and bottom layers 62 and 64 of a suitable ferroelectric ceramic, separated by a metal foil 66. As is conventional, electrical leads are connected to the ceramic elements 62 and 64 and upon applying a reversing electical voltage, the element 40 will alternately be flexing upwardly and downwardly into a convex and concave shape to provide a displacement for providing the motive force for the power supply required. It has been calculated that the four piezoelectric elements shown in FIG. 1 having a length of 7 inches, a width of 3 inches and a thickness of ¼ inch will deflect sufficiently with a force to provide a hydraulic flow rate of at least eight liters per minute at a frequency in the range of 60 to 100 cycles per minute and with a pressure of at least 150 mm of Hg. Such a power output is sufficient to drive an artificial heart directly, when 400 volts is applied thereto, without the necessity of valves or other extraneous equipment to transpose the piezoelectric drive system output to a level needed to actuate the blood flow in a human.

Another feature of the present invention is wherein the piezoelectric drive system includes an electrical circuit which not only conveniently provides electrical power to the piezoelectric elements in a convenient and efficient package, but provides means for recapturing and reusing some of the electrical power driving the piezoelectric elements instead of merely discharging the power to ground. Referring now to FIG. 10, one of the piezoelectric elements such as 40 is indicated schematically in electrical form as consisting of two condensers in which their plates are one of the ceramic elements 62 and 64, respectively, and their other is the metal foil 66. Preferably, the power supply includes a battery 70 whereby the total or partially implantable system may allow an individual freedom of movement without a tether. Instead of a bulky transformer or generator, a DC to DC converter 72 is connected to the battery which steps up the voltage such as to 400 volts for actuation of the element 40. A switch 74 is provided, such as a transistor, for alternating the voltage on the piezoelectric element at the desired frequency suitable for a human heart such as in the range of 60 to 120 cycles per minute. The switch 74 is controlled by a logic control module 76. While piezoelectric devices have a very low power consumption, it is advantageous to reduce the power consumption as much as possible thereby extending the life of the battery 70 without recharging. Therefore, the control circuit is provided for means for recapturing the reusing the power driving the piezoelectric elements 40 as the voltage is reversed on the element 40 instead of merely draining the charge to the ground. For example, a resistor 78 may be provided in the electrical line to the metal foil 66, or separate resistors may be provided in the lines to the ceramic elements 62 and 64. In any event, the resistor 70 is connected across a capacitor 80 thereby allowing the discharging elements 40 to create a voltage across the resistor 78 which is supplied to the capacitor 80 for using the discharge to assist in charging the next cycle.

Generally, the output from a piezoelectric element conventionally sinusoidal. However, the wave shape of a normal heart is non-sinusoidal and is generally in the wave form as shown in FIG. 11. It is preferable that the logic control 76 in FIG. 10 operate the transistor switch 74 in the linear range to produce a wave form of the shape shown in FIG. 12 to more nearly simulate the normal wave form shown in FIG. 11 than a sinusoidal wave form.

While the check valves 14, 16, 18 and 20 shown in FIG. 1 may be of any suitable type, a preferred type of valve is best seen in FIGS. 8 and 9. The valve 14 of FIG. 8 is similar to the valve 16 of FIG. 9, but merely reverse. Each of the valves includes a valve seat 90 and a flexible valve element 92. The valve 92 may be made out of any suitable material such as polyurethane. Preferably the valve 92 is circular and includes two supporting tabs 94. The tabs 94 are connected to opposite sides of the valve element 92 and connected to the valve seat 90. The valve 92 has an advantage over a conventional cantilevered type valve element in that the two tabs 94 provide additional support for preventing the valve element 92 from being pushed through the valve seat 90 and getting stuck in restricting flow. Preferably, the valve seat 90 is angled upwardly towards the valve 92, and the valve 92 increases in thickness from its point of flexture 95 towards its outer edges 97. This allows the valve to be flexible to open easily but reduces the possibility of the valve 92 being pushed through the seat 90 opening on the reverse cycle.

The present invention, therefore, is well adapted to carry out the objects and attain the ends and advantages mentioned as well as others inherent therein. While presently preferred embodiments of the invention have been given for the purpose of disclosure, numerous changes in the details of construction and arrangement of parts will be readily apparent to those skilled in the art and which are encompassed within the spirit of the invention and the scope of the appended claims.

What is claimed is:

1. An implantable blood pump comprising,
an artificial heart,
a hydraulic bladder connected to the exterior of the artificial heart for contracting and releasing the heart in response to hydraulic pressure,
a hydraulic pump connected to the hydraulic bladder, and
a valveless piezoelectric drive system connected to and driving the hydraulic pump, said system having a frequency in the range of 60 to 120 cycles per minute and providing a hydraulic flow rate of 8 liters per minute.

2. The apparatus of claim 1 including,
a battery and a DC to DC converter connected between the battery and the piezoelectric drive system.

3. The apparatus of claim 2 including,
means for recapturing and reusing the power driving the piezoelectric drive system.

4. The apparatus of claim 1 wherein said artificial heart includes first and second check valves, and
each valve includes a valve seat, a flexible valve element, and two supporting tabs, said tabs connected to opposite sides of the valve element and connected to the valve seat.

5. The apparatus of claim 4 wherein the valve elements are circular, and increase in thickness from the center to the outer periphery.

6. A fluid delivery system for use in the human body comprising,
a hydraulic bladder,
a hydraulic pump connected to the hydraulic bladder,
a valveless piezoelectric drive system connected to and driving the hydraulic pump, and
means in the drive system for recapturing and reusing the electric power driving the piezoelectric drive system.

7. The apparatus of claim 6 wherein the power recapturing and reusing means includes,
a resistor connected across a capacitor.

8. The apparatus of claim 6 including,
control means actuating the drive system, said control means including switching means providing an output pressure wave shape simulating a heart wave shape.

9. An implantable blood pump comprising,
an artificial heart having check valves, and
a valveless piezoelectric drive system connected directly to the exterior of the heart, said system having a frequency in the range of 60 to 120 cycles per minute and providing an output sufficient to create a blood flow rate of 8 liters per minute.

10. The apparatus of claim 9 including,
a battery and a DC to DC converter connected between the battery and the piezoelectric drive system.

11. The apparatus of claim 10 including,
means for recapturing and reusing the power driving the piezoelectric drive system.

12. The apparatus of claim 9 wherein said piezoelectric drive system includes an elongate piezoelectric plates on opposite sides of the heart.

13. The apparatus of claim 9 wherein said piezoelectric drive system includes,
a plurality of piezoelectric fibers encircling said heart and positioned parallel to each other.

14. The apparatus of claim 9 wherein said artificial heart includes first and second check valves, and
each valve includes a valve seat, a flexible valve element, and two supporting tabs, said tabs connected to opposite sides of the valve element and connected to the valve seat.

15. The apparatus of claim 14 wherein the valve elements are circular.

16. An implantable pump for actuating a human heart comprising,
a hydraulic bladder for surrounding the exterior of the heart for contracting and releasing the heart in response to hydraulic pressure,
a hydraulic pump connected to the hydraulic bladder, and
a valveless piezoelectric drive system connected to and driving the hydraulic pump, said system having a frequency in the range of 60 to 120 cycles per minute and providing a blood pumping flow rate of 8 liters per minute.

17. The apparatus of claim 16 including,
a battery and a DC to DC converter connected between the battery and the piezoelectric drive system.

18. The apparatus of claim 17 including,
means for recapturing and reusing the power driving the piezoelectric drive system.

* * * * *